US00PP11969P2

(12) United States Plant Patent
Persoff

(10) Patent No.: US PP11,969 P2
(45) Date of Patent: Jul. 3, 2001

(54) MIMULUS PLANT NAMED 'JELLY BEAN WHITE'

(76) Inventor: Richard Persoff, 1712 Dayton Ave., Alameda, CA (US) 94501

( * ) Notice: Subject to any disclaimer, the term of this patent is extended or adjusted under 35 U.S.C. 154(b) by 0 days.

(21) Appl. No.: 09/606,125

(22) Filed: Jun. 28, 2000

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—C. A. Whealy

(57) ABSTRACT

A distinct cultivar of Mimulus plant named 'Jelly Bean White', characterized by its upright, rounded and compact plant habit, freely branching habit; moderate vigor; dark green leaves; and numerous large white ruffled flowers.

2 Drawing Sheets

BACKGROUND OF THE INVENTION

The present invention relates to a new and distinct cultivar of Mimulus plant, botanically known as *Mimulus aurantiacus,* and hereinafter referred to by the cultivar name Jelly Bean White.

The new Mimulus is a product of a planned breeding program conducted by the Inventor in Alameda, Calif. The new Mimulus originated from a cross made by the Inventor of two unidentified selections of *Mimulus aurantiacus*. The new Mimulus was selected in 1999 on the basis of its compact and freely flowering habit.

Asexual reproduction of the new cultivar by terminal cuttings taken at Alameda, Calif., has shown that the unique features of this new Mimulus are stable and reproduced true to type in successive generations.

SUMMARY OF THE INVENTION

Plants of the cultivar Jelly Bean White have not been observed under all possible environmental conditions. The phenotype may vary somewhat with variations in environment such as temperature, light intensity, daylength, and nutritional status without, however, any variance in genotype.

The following traits have been repeatedly observed and are determined to be the unique characteristics of 'Jelly Bean White'. These characteristics in combination distinguish 'Jelly Bean White' as a new and distinct cultivar:

1. Upright, rounded and compact plant habit.
2. Freely branching habit.
3. Moderate vigor.
4. Dark green leaves.
5. Numerous large ruffled white flowers with light yellow throat.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Mimulus.

The photograph on the first sheet comprises a side perspective view of a typical flowering plant of 'Jelly Bean White' grown in a 15-cm container.

The photograph at the top of the second sheet is a close-up view of typical flowering stems of 'Jelly Bean White'.

The photograph at the bottom of the second sheet is a close-up view of typical flowers and the upper and lower surface of typical leaves of 'Jelly Bean White'.

DETAILED BOTANICAL DESCRIPTION

In the following description, color references are made to The Royal Horticultural Society Colour Chart except where general terms of ordinary dictionary significance are used. Plants grown in 15-cm containers were used for the following description with one plant per container. Plants were grown in polyethylene-covered greenhouses and under conditions which closely approximate commercial production conditions during the spring in Encinitas, Calif. Day temperatures averaged about 18° C., night temperatures averaged about 10° C., and light levels were about 5,000 to 6,000 foot-candles.

Botanical classification: *Mimulus aurantiacus* cultivar Jelly Bean White.

Parentage:

*Female parent.*—Unidentified selection of *Mimulus aurantiacus*, (unpatented).

*Male parent.*—Unidentified selection of *Mimulus aurantiacus*, (unpatented).

Propagation:

*Type cutting.*—Terminal vegetative cuttings.

*Time to initiate roots, summer.*—About 14 days at 20° C.

*Root description.*—Numerous, fine.

Plant description:

*Form.*—Mostly upright, rounded and compact plant habit.

*Usage.*—Appropriate for 15-cm containers.

*Crop time.*—About 18 weeks are required to produce finished flowering plants in 15-cm containers.

*Plant height.*—About 28 cm.

*Area of spread.*—About 27 cm.

*Vigor.*—Moderately vigorous.

*Branching habit.*—Freely branching with about four lateral branched per plant; removal of terminal apices (pinching) enhances branching.

*Lateral branches.*—Length: About 18.5 cm. Diameter: About 3 cm. Internode length: About 4 cm. Texture: Slightly viscid; glabrous. Color: 144D becoming 177B with development.

*Foliage description.*—Leaves simple, generally symmetrical and long persisting; opposite. Quantity per lateral branch: Typically about 14 to 16. Length: About 5.5 cm. Width: About 1.75 cm. Aspect: Slightly reflexed. Shape: Elliptic. Apex: Rounded acute. Base: Attenuate. Margin: Entire with ciliation. Texture: Viscid; glabrous; leathery. Color: Young foliage, upper surface: 144A; somewhat glossy. Young foliage, lower surface: 144B. Mature foliage, upper surface: 147A; somewhat glossy; venation, 147A. Mature foliage, lower surface: 147B to 147C; venation, 147B. Petiole: Length: About 5 mm. Diameter: About 4.5 mm. Color: 144B.

Flower description:

*Flower type and habit.*—Large-sized flowers; flowers face mostly outward; single, axillary; salverform, zygomophic. Flowers persistent.

*Natural flowering season.*—Flowering typically from early spring until fall; about 10 weeks from planting to flowering.

*Quantity.*—Freely and continuous flowering; typically about 50 flower buds and opened flowers per plant.

*Fragrance.*—Not detected.

*Flower longevity on the plant.*—About 3 days.

*Flower buds* (*showing color*).—Length: About 3 cm. Diameter: About 1.2 cm. Shape: Elongate. Color: 155A to 155B.

*Corolla.*—Arrangement/appearance: Five-parted, fused into a tube; lobes, flared. Flower diameter: Vertical axis, about 5 cm; horizontal axis, about 4.5 cm. Flower depth (length): About 5.5 cm. Petal length: About 5.9 cm. Petal width: About 1.5 cm. Petal shape: Fan-shaped; lobes irregularly sinuate, reflexed and ruffled. Texture: Smooth, satiny. Color: Petal, upper surface, when opening: More white than 155D. Petal, lower surface, when opening: 155A. Petal, upper surface, opened flower: More white than 155D. Petal, lower surface, opened flower: 158A. Flower throat (inside): Light yellow, 2C and 2D. Flower tube (outside): 158A.

*Sepals.*—Quantity: Five, fused. Shape: Elliptic; folded at midveins; calyx, zygomorphic tube. Calyx length: About 3 cm. Calyx diameter: About 1 cm. Apex: Acute. Margin: Entire. Texture: Smooth; slightly viscid. Color: Upper surface: 144D. Lower surface: 144A to 144B.

*Peduncle.*—Strength: Good. Angle: Somewhat upright to nearly horizontal, about 55 to 90° to the stem. Length: About 8 mm. Color: 144C.

*Reproductive organs.*—Stamens: Quantity: Four total, two shorter than the other two. Anther shape: Ovoid. Anther size: About 2 by 1 mm. Anther color: 17A. Pollen amount: Scarce. Pollen color: 17B. Pistils: Pistil quantity per flower: One. Pistil length: About 3.8 cm. Stigma shape: Anvil-shaped, becoming trilobed. Stigma color: 155A. Style length: About 3.4 cm. Style color: 155A. Ovary color: 144B.

*Seed.*—Seed production has not been observed.

Disease resistance: Plants of the new Mimulus have not been noted to be resistant to pathogens common to Mimulus.

It is claimed:

1. A new and distinct cultivar of Mimulus plant named 'Jelly Bean White', as illustrated and described.

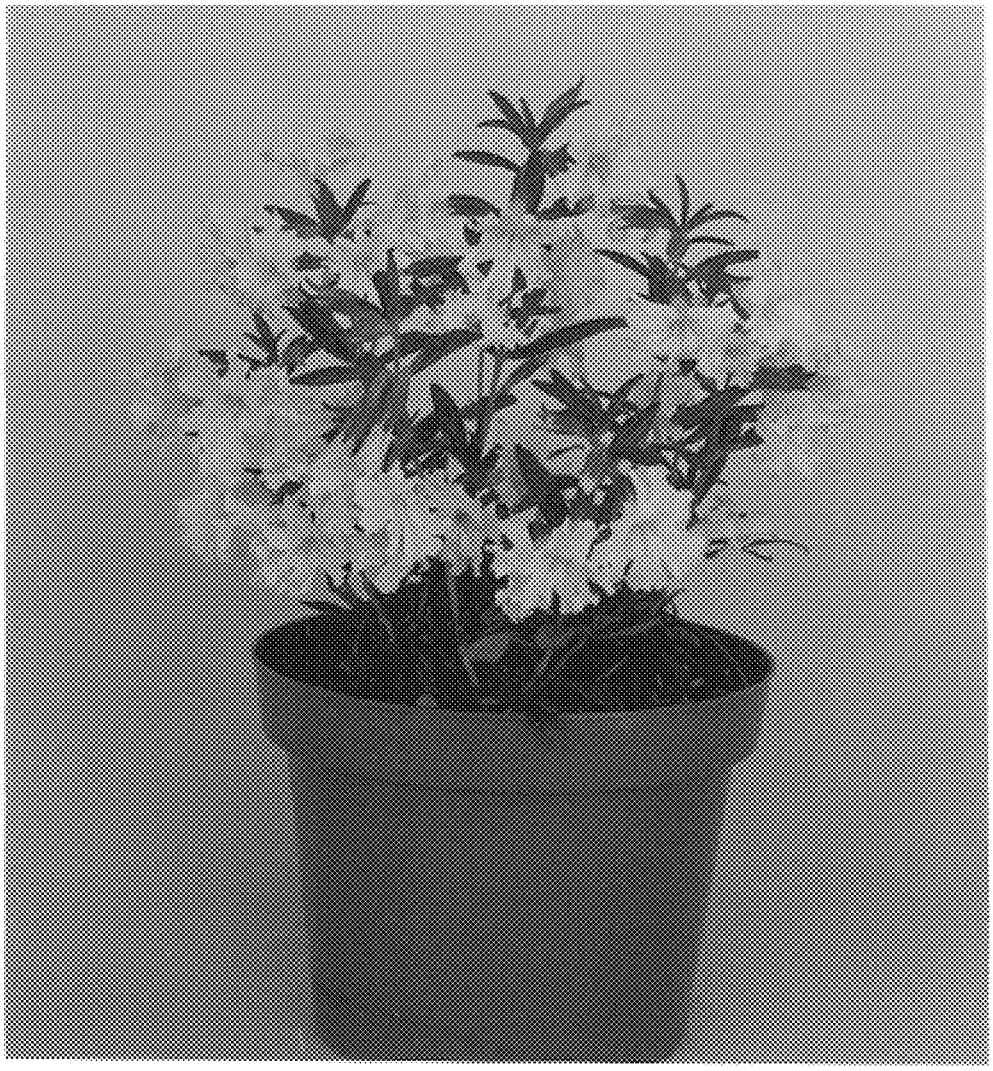

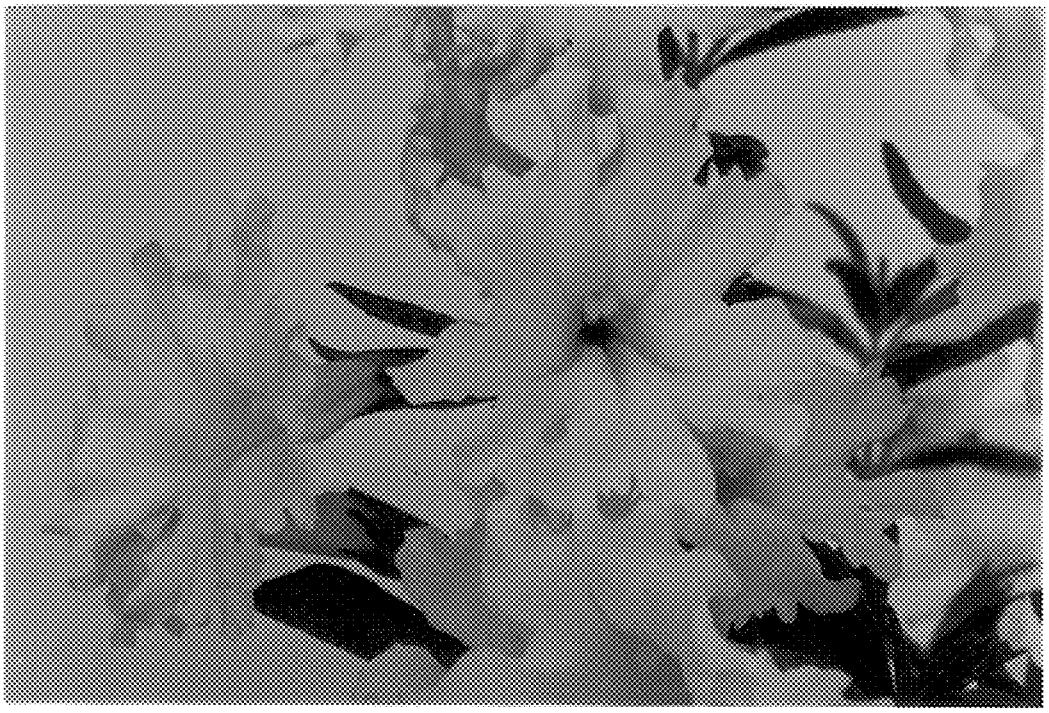
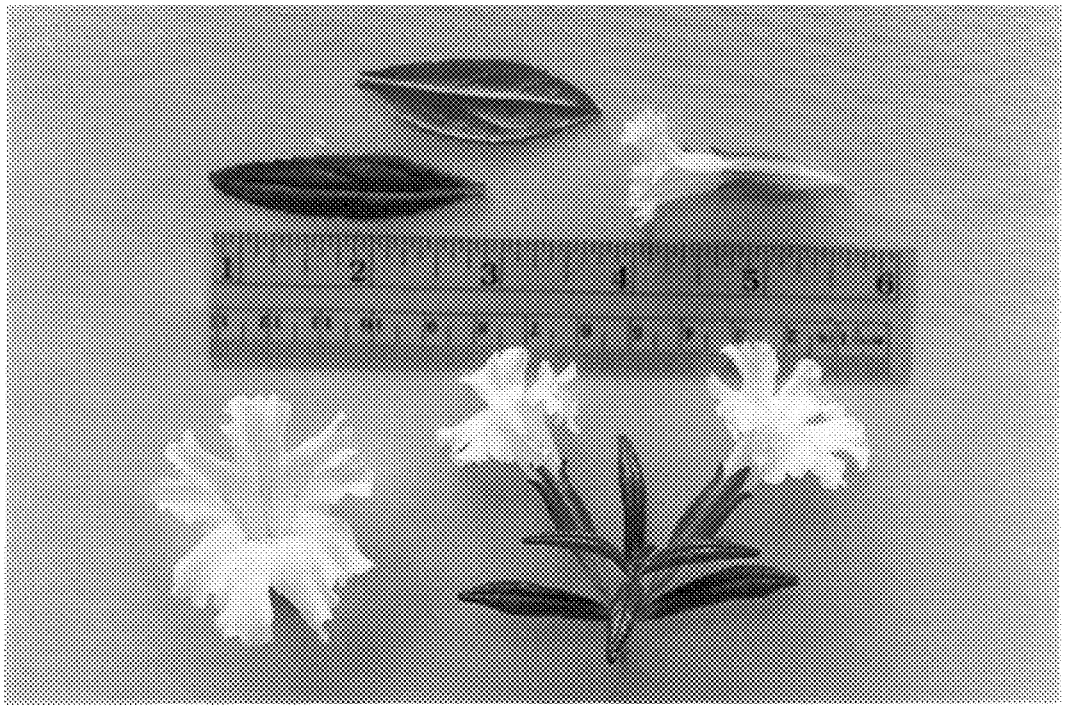

* * * * *